(12) United States Patent
Bai et al.

(10) Patent No.: US 9,157,861 B2
(45) Date of Patent: Oct. 13, 2015

(54) SENSOR AND METHOD OF DETECTING A TARGET ANALYTE

(71) Applicant: Agency for Science, Technology and Research, Singapore (SG)

(72) Inventors: Ping Bai, Singapore (SG); Xiaodong Zhou, Singapore (SG); Lin Wu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 298 days.

(21) Appl. No.: 13/665,033

(22) Filed: Oct. 31, 2012

(65) Prior Publication Data

US 2013/0112857 A1 May 9, 2013

(30) Foreign Application Priority Data

Nov. 3, 2011 (SG) .............................. 201108104-9

(51) Int. Cl.
*H01J 40/14* (2006.01)
*G01N 21/64* (2006.01)
*G01N 21/62* (2006.01)

(52) U.S. Cl.
CPC .............. *G01N 21/648* (2013.01); *G01N 21/62* (2013.01)

(58) Field of Classification Search
CPC ........ G01N 21/62; G01N 21/63; G01N 21/75
USPC ................ 250/216, 221, 222.1, 458.1, 461.2; 422/68.1, 82.05; 436/501
See application file for complete search history.

(56) References Cited

U.S. PATENT DOCUMENTS

| 8,094,314 | B2 | 1/2012 | Tetz et al. | |
| 2003/0132392 | A1* | 7/2003 | Kuroda et al. | 250/397 |
| 2006/0273245 | A1* | 12/2006 | Kim et al. | 250/226 |
| 2013/0029430 | A1* | 1/2013 | Tamura et al. | 436/501 |

OTHER PUBLICATIONS

Erickson, et al., Nanobiosensors: Optofluidic, Electrical and Mechanical Approaches to Biomolecular Detection at the Nanoscale, Microfluid Nanofluid, 33 (2008).

* cited by examiner

*Primary Examiner* — Kevin Pyo
(74) *Attorney, Agent, or Firm* — K. David Crockett, Esq.; Niky Economy Syrengelas, Esq.; Crockett & Crockett, PC

(57) ABSTRACT

A sensor and a method of detecting a target analyte are provided. The sensor includes a substrate; a layer comprising a plurality of through holes, wherein the layer is disposed above the substrate; a first element configured to detect a target analyte; a second element that can produce a detectable signal; wherein the first element and the second element are configured to couple the target analyte between the first element and the second element.

17 Claims, 15 Drawing Sheets

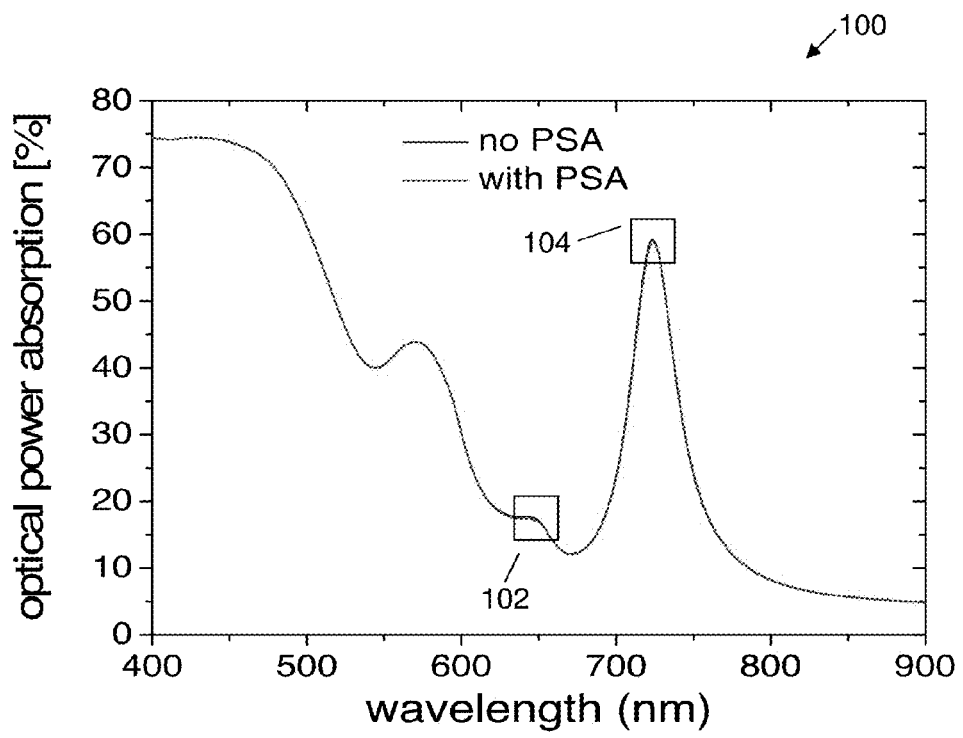
FIG. 1a
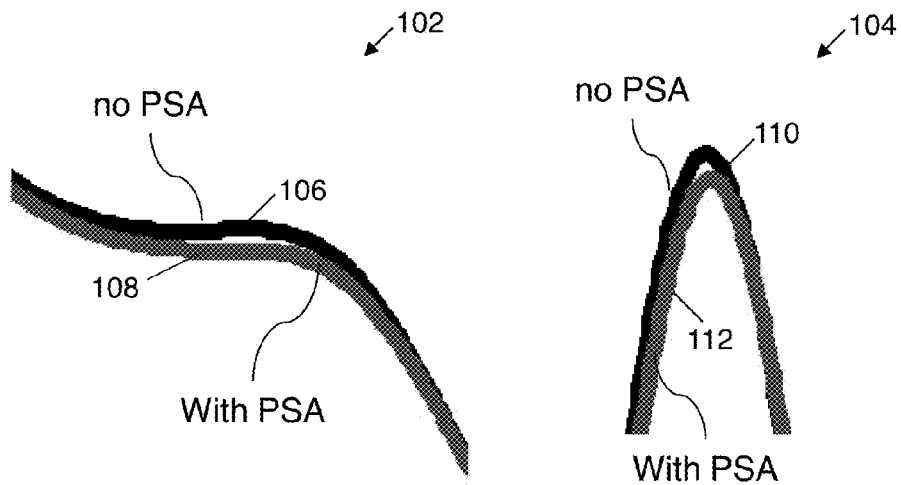
FIG. 1b
FIG. 1c

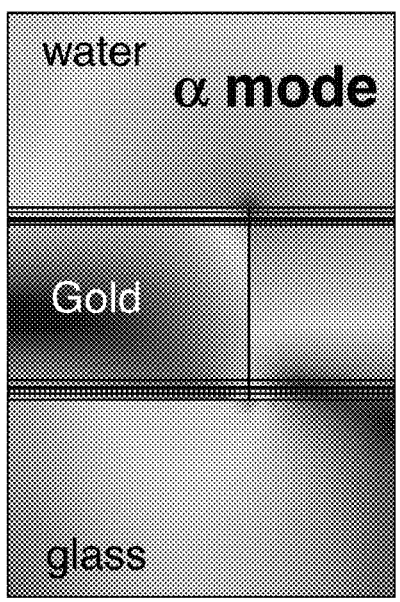 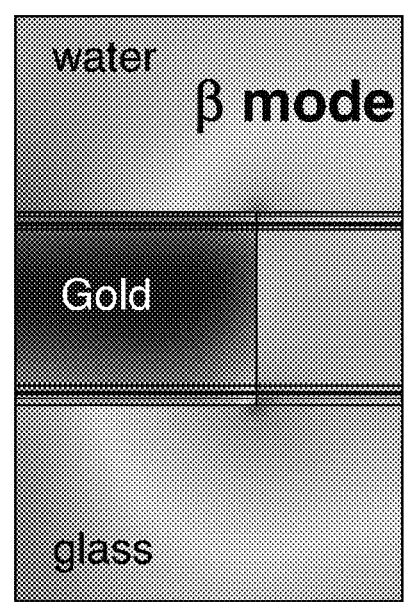
FIG. 5a                    FIG. 5b

SENSOR AND METHOD OF DETECTING A TARGET ANALYTE

CROSS-REFERENCE TO RELATED APPLICATION

This application claims the benefit of priority of Singapore Patent Application No. 201108104-9, filed Nov. 3, 2011, the contents of which are incorporated herein by reference for all purposes.

TECHNICAL FIELD

Various embodiments relate generally to a sensor and a method of detecting a target analyte.

BACKGROUND

Surface plasmon resonance (SPR) is a conventional method to measure binding stoichiometry, kinetics, and chemical affinity. The principle of SPR is based on the interaction between light and conductive electrons at a surface of a metal film including silver, gold, aluminum or copper. When a resonant condition is fulfilled and surface plasmon is generated on the surface of the metal film, the detected light shows a peak at the resonance wavelength (in spectral interrogation) or at the resonance angle (in angular interrogation). This resonance peak will shift according to the reflective index variation on the surface of the metal film caused by the analyte binding. Thus, it gives the real-time information of the binding events. The kinetics, the affinities and the concentrations of the analyte can be calculated as the dynamic process saturates with time.

However, conventional SPR sensors require apparatuses such as a prism to adjust the momentum of the light so as to match with the momentum of the electrons in the metal film to induce the plasmonic resonance. These conventional sensors are generally very bulky. It is difficult to develop such conventional sensors into a point-of-care sensing system.

Localized surface plasmon resonance (LSPR), which utilizes the interaction between the light and the metal nanostructures, has also been used. LSPR has similar functions as SPR, and LSPR can be generated by directly illuminating the light at any angle onto a metal nanostructure with a dielectric interface. Thus, a portable LSPR biosensing system can be realized. However, it is difficult for LSPR sensors to detect a small molecule (in a nanometer range), as the small molecules cause very little peak shift.

FIG. 1a shows a graph 100 of optical power absorption against wavelength for prostate cancer biomarker prostate-specific antigen (PSA) in blood. Graph 100 shows an absorption spectrum of a gold nanohole array (without the PSA), and an absorption spectrum of the gold nanohole array with the PSA. The gold nanohole array has a thickness of about 100 nm and a pitch of about 400 nm. The diameter of each nanohole of the array is about 150 nm. The diameter of the PSA is about 1 nm.

FIGS. 1b and 1c show magnifications of portion 102 and portion 104 of graph 100. FIG. 1b shows a portion 106 of the absorption spectrum of the gold nanohole array (without the PSA), and a portion 108 of the absorption spectrum of the gold nanohole array with the PSA. FIG. 1c shows a portion 110 of the absorption spectrum of the gold nanohole array (without the PSA), and a portion 112 of the absorption spectrum of the gold nanohole array with the PSA. It can be observed from both FIGS. 1b and 1c that the PSA only causes a negligible resonant change in the absorption spectrum of the gold nanohole array, which needs a highly accurate spectrometer to discern the difference.

SUMMARY

According to one embodiment, a sensor is provided. The sensor includes a substrate; a layer comprising a plurality of through holes, wherein the layer is disposed above the substrate; a first element configured to detect a target analyte; a second element that can produce a detectable signal; wherein the first element and the second element are configured to couple the target analyte between the first element and the second element.

According to another embodiment, a method of detecting a target analyte is provided. The method includes coupling the target analyte between a first element and a second element; wherein the first element detects the target analyte and the second element produces a detectable signal in response to an excitation of the second element coupling to the target analyte.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 1a shows a graph of optical power absorption against wavelength for prostate cancer biomarker prostate-specific antigen (PSA) in blood.

FIGS. 1b and 1c show magnifications of respective portions of the graph of FIG. 1a.

FIGS. 5a and 5b show electric field distribution for surface plasmon modes $\alpha$ and $\beta$ respectively according to one embodiment.

DETAILED DESCRIPTION

Embodiments of a sensor and a method for detecting a target analyte will be described in detail below with reference to the accompanying figures. It will be appreciated that the embodiments described below can be modified in various aspects without changing the essence of the invention.

Figure 2A:
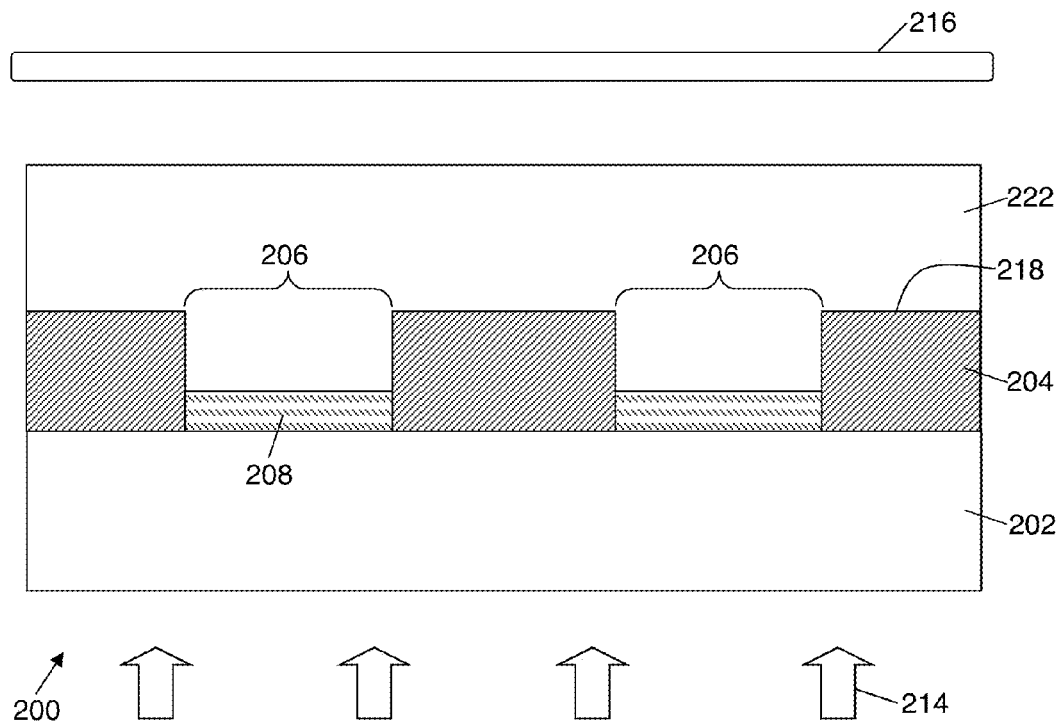
FIG. 2a shows a cross-sectional view of a sensor according to one embodiment.
Figure 2B:
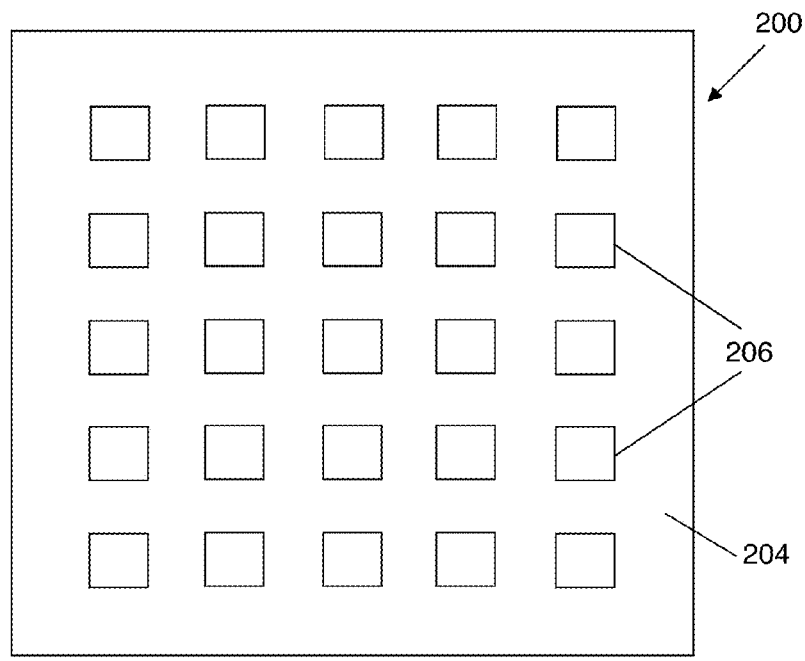
FIG. 2b shows a top view of a sensor according to one embodiment.

FIG. 2a shows a cross-sectional view of a sensor 200 according to one embodiment. FIG. 2b shows a top view of the sensor 200. The sensor 200 includes a substrate 202, a layer 204 having a plurality of through holes 206 and a first element 208. In one embodiment, the layer 204 is disposed above the substrate 202. The first element 208 may be disposed adjacent the layer 204. The first element 208 may be arranged within the through holes 206 of the layer 204.

In one embodiment, the substrate 202 is a support substrate for the sensor 200. The substrate 202 is transparent. The substrate 202 includes any transparent materials. Examples of the transparent material include but are not limited to glass and quartz. The substrate 202 may have a length ranging from hundreds of micrometers to a few centimeters, a width ranging from hundreds of micrometers to a few centimeters and a thickness ranging from micrometers to a few millimeters. In one embodiment, the substrate 202 may have a length ranging from about 100 μm to about 1 cm, a width ranging from about 100 μm to about 1 cm, and a thickness ranging from about 50 μm to about 2 mm. For example, the substrate 202 may have a length of about 5 mm, a width of about 5 mm, and a thickness of about 600 μm. A larger substrate may be used for a single channel configuration as a larger substrate provides ease for handling. A smaller substrate may be used for multi-channels configuration.

In one embodiment, the layer 204 includes metal. Examples of the metal include but are not limited to silver, gold and aluminum. The layer 204 may have a length ranging from tens of micrometers to a few centimeters, a width ranging from tens of micrometers to a few centimeters and a thickness ranging from tens of nanometers to hundreds of nanometers. In one embodiment, the layer 204 may have a length ranging from about 10 μm to about 1 cm, a width ranging from about 10 μm to about 1 cm, and a thickness ranging from about 10 nm to about 300 nm. For example, the layer 204 may have a length of about 3 mm, a width of about 3 mm, and a thickness of about 90 nm. In one embodiment, the size of the layer 204 may be smaller than the size of the substrate 202. For example, an area of the layer 204 may be smaller than an area of the substrate 202. In another embodiment, the layer 204 and the substrate 202 may have the same size. For example, the layer 204 and the substrate 202 may have the same area. In other words, the layer 204 disposed above the substrate 202 may cover the whole area of the substrate 202. The through holes 206 can have various shapes. For example, the through holes 206 may be circular, triangular, square, polygonal, etc. In one embodiment, the through holes 206 of the layer 204 may have the same shape. In another embodiment, the through holes 206 of the layer 204 may have different shapes (e.g. any combinations of shapes on one layer 204). The through holes 206 may be distributed sequentially (e.g. having a certain order) or randomly. A feature size (e.g. diameter) of the through holes 206 may be smaller than a wavelength of a light directed to the sensor 200. The feature size (e.g. diameter) of the through holes 206 may range from tens of nanometers to a few micrometers, depending on the wavelength of the light directed to the sensor 200. In one embodiment, the feature size (e.g. diameter) of the through holes 206 may range from about 10 nm to about 800 nm. The feature size (e.g. diameter) of the through holes 206 may range from about 50 nm to about 400 nm. For example, the feature size (e.g. diameter) of the through holes 206 may be about 150 nm. A depth of the through holes 206 and the thickness of the layer 204 may be the same.

In one embodiment, the first element 208 may be a molecular recognition element which recognizes and captures a target analyte in a matrix. In other words, the first element 208 may be configured to detect a target analyte in a matrix. The first element 208 may include one or more materials. The materials chosen for the first element 208 depend on the properties of the target analyte to be detected. A thickness of the first element 208 may be designed to position the target analyte at locations where electromagnetic field is maximally enhanced.

It can be understood that 'target analyte' (e.g. target analyte 220 shown in FIG. 2c) refers to target molecules to be detected. The target molecules can be any molecules of dietary, environmental or biomedical interest, depending on the particular application. It can also be understood that 'matrix' refers to where the target analyte resides. The matrix is generally liquid.

Figure 2C:
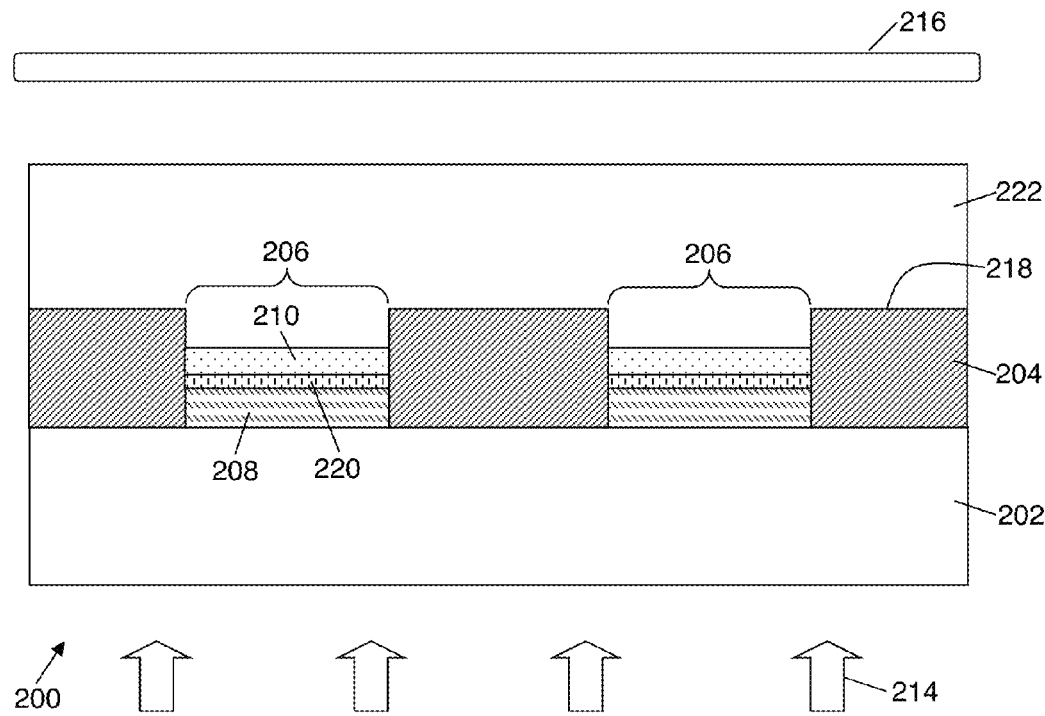
FIG. 2c shows a cross-sectional view of a sensor according to one embodiment.

The sensor 200 further includes a second element 210 as shown in FIG. 2c. In one embodiment, the second element 210 may be arranged within the through holes 206 of the layer 204. The second element 210 can produce a detectable signal.

In one embodiment, the second element 210 may include a label (not shown). The label may include but is not limited to fluorescence dye or light emitter. The second element 210 may further include a linker (not shown) configured to couple the label to a target analyte. The linker may be a complementary part of a target analyte. For example, if the target analyte is a prostate-specific antigen (PSA), the linker can be a PSA antibody.

The sensor 200 further includes a light source 214 and an optical detector 216. In one embodiment, the light source 214 can be any kind of source which can emit white light with a wavelength ranging from about 400 nm to about 800 nm. The light source 214 can be positioned anywhere around the metal film. In one embodiment, the light source 214 may be disposed at a side of the sensor 200 facing the substrate 202. In another embodiment, the source 214 may be disposed at a side of the sensor 200 facing away from the substrate 202.

The optical detector 216 may include but is not limited to a photodetector or a camera. In one embodiment, the optical detector 216 may be disposed at an opposite side of the sensor 200 away from the light source 214. In another embodiment, the optical detector 216 and the light source 214 may be disposed at the same side of the sensor 200.

In one embodiment, the sensor 200 is a plasmonic sensor.

Details of how the sensor 200 operates are described in the following.

In one embodiment, the light source 214 directs light to the sensor 200. In other words, the light source 214 illuminates the sensor 200 including the layer 204. The layer 204 may generate localized surface plasmon resonance (LSPR) near a surface 218 of the layer 204. Electromagnetic field or plasmonic signal near the surface 218 of the layer 204 may be enhanced.

If a target analyte 220 is present in a matrix 222 as shown in FIG. 2c, the first element 208 may detect the target analyte 220. The second element 210 may also detect the target analyte 220 in the matrix 222. The first element 208 and the second element 210 may couple the target analyte 220 between the first element 208 and the second element 210. The first element 208, the target analyte 220 and the second element 210 may form a (first element 208)-target analyte 220-(second element 210) sandwich structure.

Figure 2D:
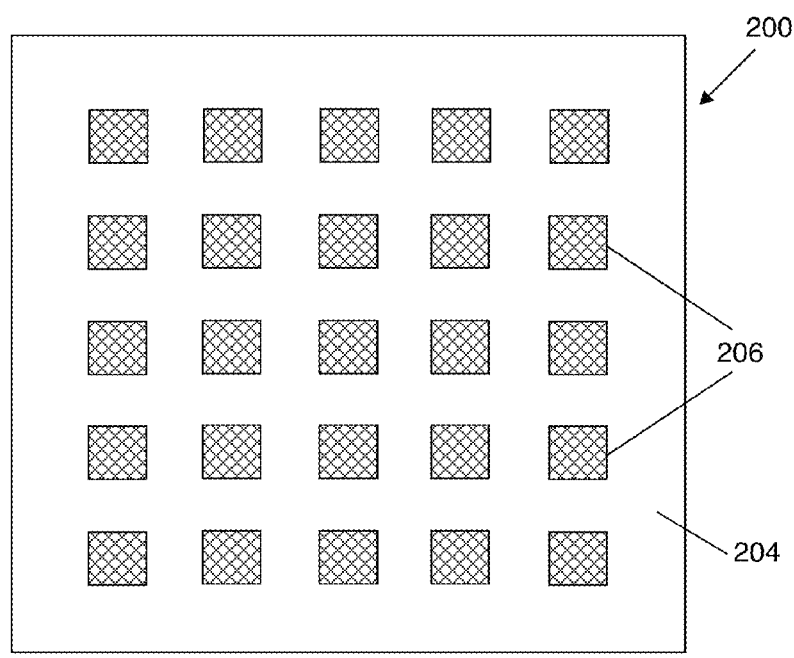
FIG. 2d shows a top view of a sensor according to one embodiment.

FIG. 2d shows a top view of the sensor 200 illustrating the target analyte 220 coupled to the first element 208 and the second element 210 within the through holes 206 of the layer 204.

If the target analyte 220 and the second element 210 are near the layer 204, the enhanced electromagnetic field near the surface 218 of the layer 204 may excite the second element 210 to emit a detectable signal. The second element 210 may produce the detectable signal in response to an excitation of the second element 210 coupling to the target analyte 220. The second element 210 may produce the detectable signal when the second element 210 is coupled to the target analyte and when light is directed to the sensor 200 from the light source 214. The detectable signal produced by the second element 210 includes light. The optical detector 216 may detect the detectable signal produced by the second element 210.

In the event that the target analyte 220 is not present in the matrix 214, the second element 210 may be washed away. There is no second element 210 as shown in FIG. 2a. As such, the electromagnetic field enhanced by the plasmonic resonance may not be strong enough to be detected by the optical detector 216.

Therefore, the second element 210 can enhance LSPR when the target analyte 220 is present. A small molecule can then be easily detected by the sensor 200 via dark field detection. The sensor 200 can detect small molecules by using a metallic nanohole array (e.g. layer 204 having through holes 206) to generate the LSPR and a selectable signal enhancement element (e.g. second element 210) to improve the detection limit. The sensor 200 can provide high sensitivity without the need for expensive optical detector and light sources, and may have the potential to be developed into a point-of-care diagnostic system.

Figure 3:
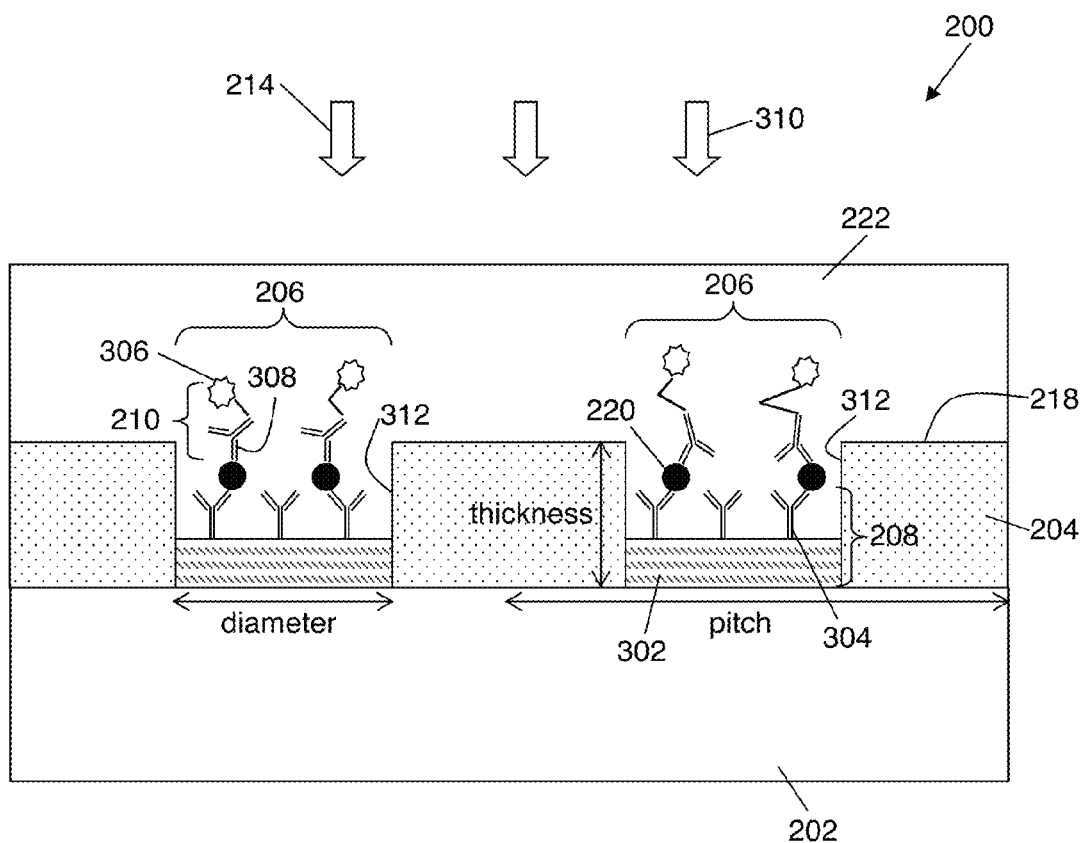
FIG. 3 shows a schematic diagram of a sensor according to one embodiment.

FIG. 3 shows a schematic diagram of the sensor 200. In one embodiment, the sensor 200 can be used for detecting prostate-specific antigen (PSA). The sensor 200 can be used for health screening or clinical management of prostate cancer. The target analyte 220 is PSA and the matrix 222 is water. The target analyte 220 may have a size of about 1 nm. The substrate 202 includes glass. The layer 204 includes gold. The layer 204 may have a thickness of about 100 nm. The through holes 206 of the layer 204 have a circular shape and are distributed sequentially. The pitch of the through holes 206 (e.g. distance between adjacent through holes 206) may be about 400 nm. The diameter of the through holes 206 may be about 150 nm.

The first element 208 includes two materials, namely a brush polymer 302 (e.g. a layer of non-fouling poly oligo ethylene glycol methacrylate (pOEGMA)) and a layer of PSA antibodies 304. The brush polymer 302 may be disposed on the substrate 202 within the through holes 206 of the layer 204. The brush polymer 302 may have a thickness of about 90 nm. The PSA antibodies 304 may be bound to the layer 204 (e.g. within the through holes 206 of the layer 204) via the brush polymer 302 and are used to detect and couple to the target analyte 220 (i.e. PSA). The layer of PSA antibodies 304 may have a thickness of about 3 nm.

The second element 210 includes fluorescence dyes as the label 306 and PSA antibodies as the linker 308. The linker 308 (e.g. PSA antibodies) may have a thickness of about 3 nm.

Light may be directed to the sensor 200 in a direction 310 perpendicular to the sensor 200 from the matrix side. In other words, the light source 214 may be arranged at the matrix side of the sensor 200 (e.g. at a side of the sensor 200 facing away from the substrate 202). The optical detector (not shown) may be disposed at the same side of the sensor 200 as the light source 214.

In one embodiment, a sensitivity of the sensor 200 is configured based on one or more of the following factors: a) a resonant wavelength of the sensor 200, b) an electric field distribution of the sensor 200, and c) a position of the second element 210. The resonant wavelength of the sensor 200 may be configured to be equal to an excitation wavelength of the second element 210. The second element 210 may be arranged at positions with the highest electric field enhancement.

Therefore, to increase the detection sensitivity of the sensor 200, it is desirable that the plasmonic resonant wavelength of the sensor 200 exactly matches the excitation wavelength of the label 306 of the second element 210, the electric field distribution of the sensor 200 is optimized or the electric field enhancement is maximized, and the label 306 of the second element 210 is positioned near the layer 204 where the electric field is enhanced the most.

Details of how plasmonic resonant wavelengths are identified are described in the following.

When the sensor 200 is exposed to a broadband illumination (e.g. light having a wavelength ranging from about 400 nm to about 800 nm), some incident optical power is reflected from the layer 204. Some is absorbed in the layer 204 and is converted into other forms of energy. The rest is transmitted through the layer 204. In theoretical study, the three parts of the optical power are calculated and the reflection, absorption, and transmission at different wavelengths are obtained. However, only the absorbed optical power is responsible for LSPR.

Figure 4:
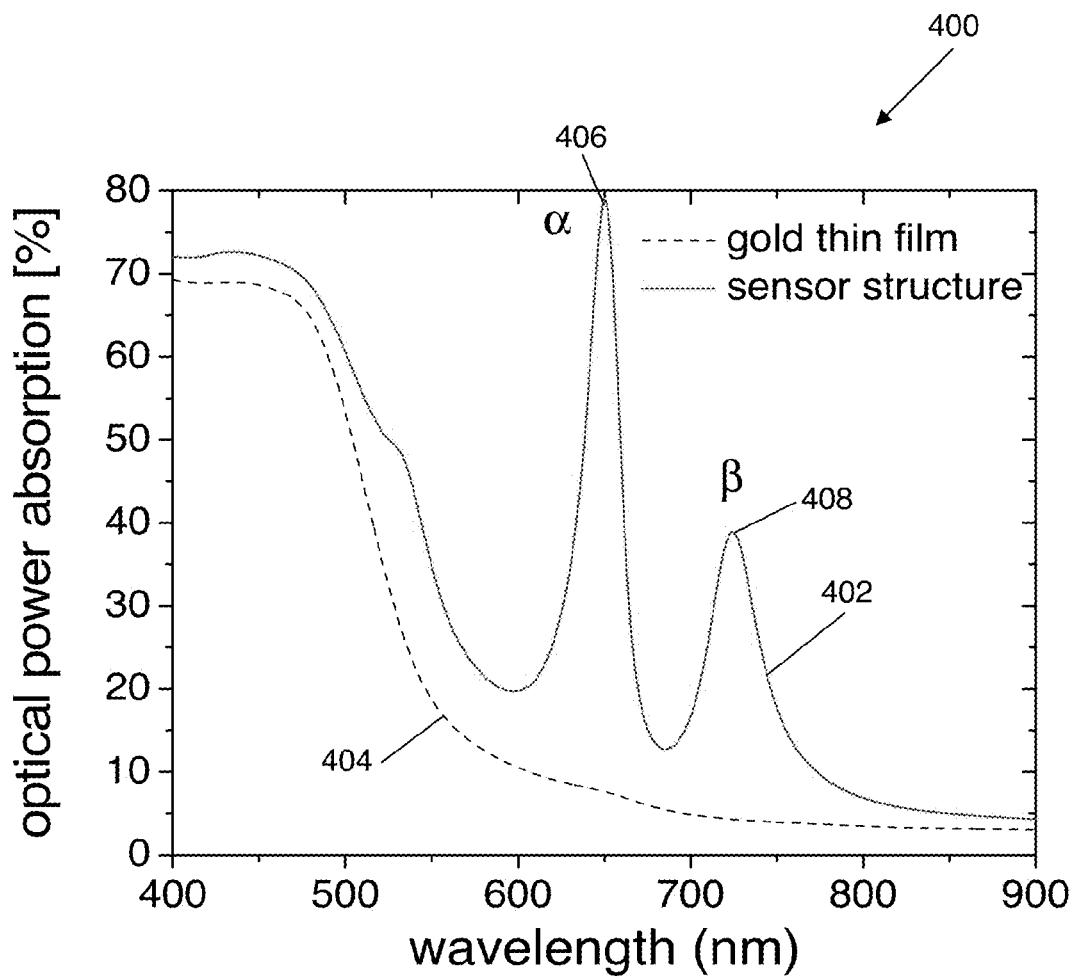
FIG. 4 shows a graph of optical power absorption plotted against wavelength according to one embodiment.

FIG. 4 shows a graph 400 of optical power absorption plotted against wavelength. Graph 400 shows an absorption spectrum 402 of the sensor 200 and an absorption spectrum 404 of a 100 nm thick gold thin film. The absorption spectrum 404 of the gold thin film is a monotonically decreasing function of the wavelength. This implies that all the absorbed optical power is bulk absorption depending on the wavelength. On the other hand, the absorption spectrum 402 of the sensor 200 exhibits two resonant peaks 406 and 408 superimposed on a monotonically decreasing line. The two resonant peaks 406 and 408 imply how much absorbed optical power is turned into LSPR.

The two resonant peaks 406 and 408 correspond to the two different surface plasmon modes α and β respectively. FIGS. 5a and 5b show electric field distribution for surface plasmon modes α and β respectively. It can be observed that for surface plasmon mode α, the LSPR concentrates mainly at a gold/matrix interface (i.e. an interface of the layer 204 and the matrix 222 (FIG. 3)), while for surface plasmon mode β, the LSPR concentrates mainly at a glass/gold interface (i.e. an interface of the substrate 202 and the layer 204 (FIG. 3)).

Since the target analyte 220 (i.e. PSA), the PSA antibodies (e.g. the PSA antibodies 304 of the first element 208 and the linker 308 of the second element 210), the fluorescence dyes (i.e. the label 306 the second element 210) are located at the gold/matrix interface, the surface plasmon mode α is defined as the principal mode and is focused for configuring the sensitivity of the sensor 200.

The resonant wavelength of the sensor 200 may be configured to be equal to an excitation wavelength of the second element 210 (in other words, the plasmonic resonant wavelength of the sensor 200 may be tuned to match the excitation wavelength of the label 306 of the second element 210) to obtain maximum optical emission of the second label. The LSPR may be dependent on the geometry of the layer 204, the material of the layer 204 and the materials around the layer 204. If the material of the substrate 202, the material of the layer 204, the analyte 220 and the matrix 222 are fixed, the geometry of the layer 204 becomes the main factor for the LSPR.

For the sensor 200 shown in FIG. 3, a pitch of the through holes 206, a size (e.g. diameter) of the through holes 206 and a thickness of the layer 204 or a depth of the through holes 206 are parameters for determining the geometry of the layer 204, and can consequently affect the LSPR. In other words, the resonant wavelength of the sensor 200 may be configured based on one or more of the following parameters: the pitch of the through holes 206, the size (e.g. diameter) of the through holes 206 and the thickness of the layer 204 or the depth of the through holes 206. Each of the parameters is varied independently to determine its effects on the resonant wavelength of the sensor 200.

Figure 6A:
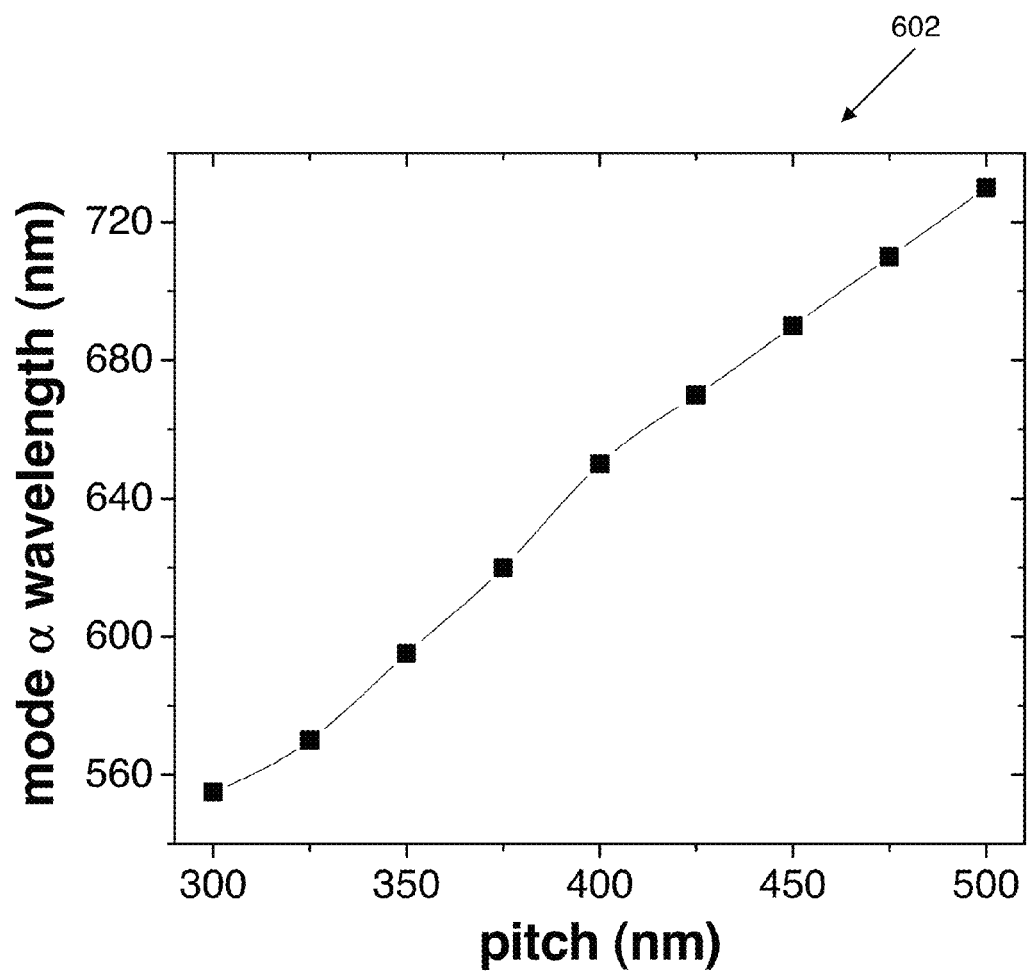
FIG. 6a shows a graph of a resonant wavelength of surface plasmon mode $\alpha$ plotted against a pitch of through holes of a layer of a sensor according to one embodiment.

FIG. 6a shows a graph 602 of a resonant wavelength of the principal mode α plotted against a pitch of the through holes 206. It can be observed from graph 602 that a 100 nm increase in the pitch results in a 90 nm increase in the resonant wavelength.

Figure 6B:
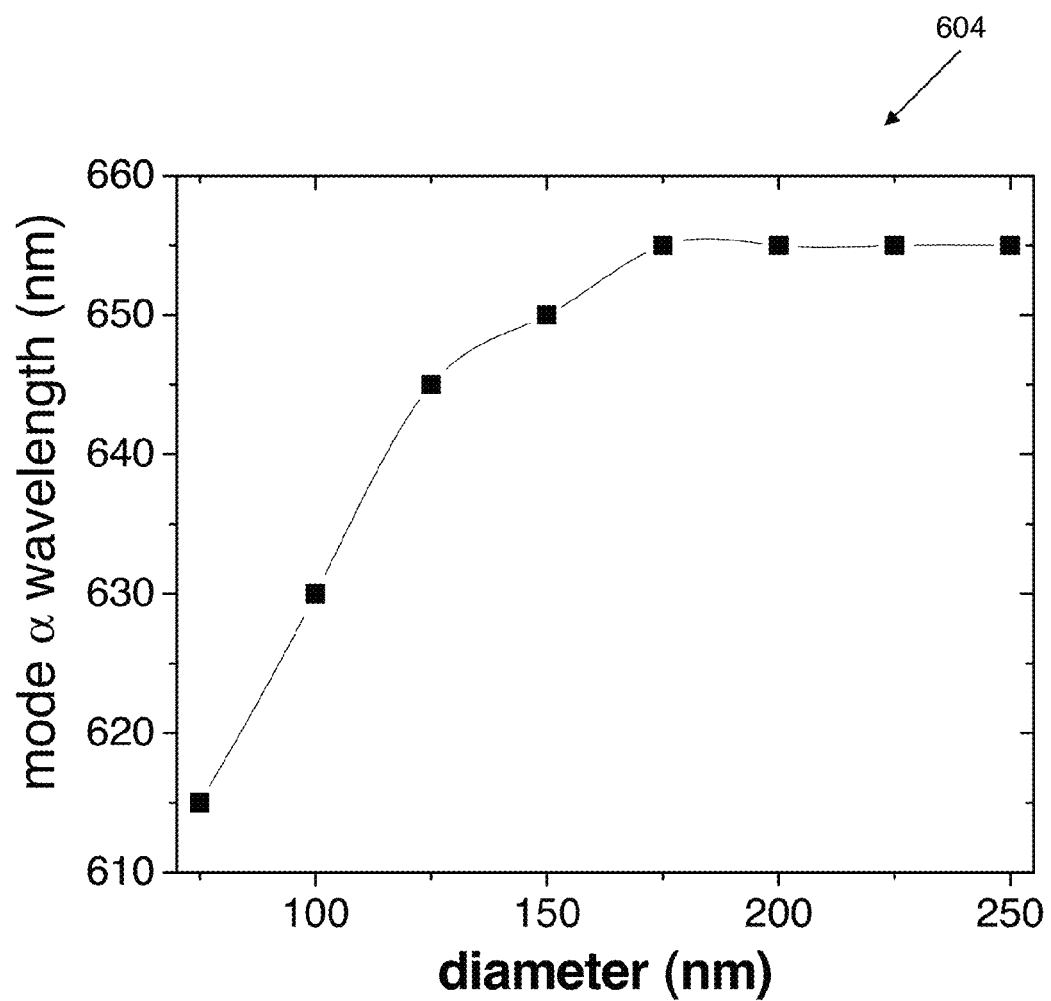
FIG. 6b shows a graph of a resonant wavelength of surface plasmon mode $\alpha$ plotted against a diameter of through holes of a layer of a sensor according to one embodiment.

FIG. 6b shows a graph 604 of the resonant wavelength of the principal mode α plotted against a diameter of the through holes 206. It can be observed from graph 604 that increasing the diameter from 75 nm to 250 nm leads to a resonant wavelength increase of 50 nm.

Figure 6C:
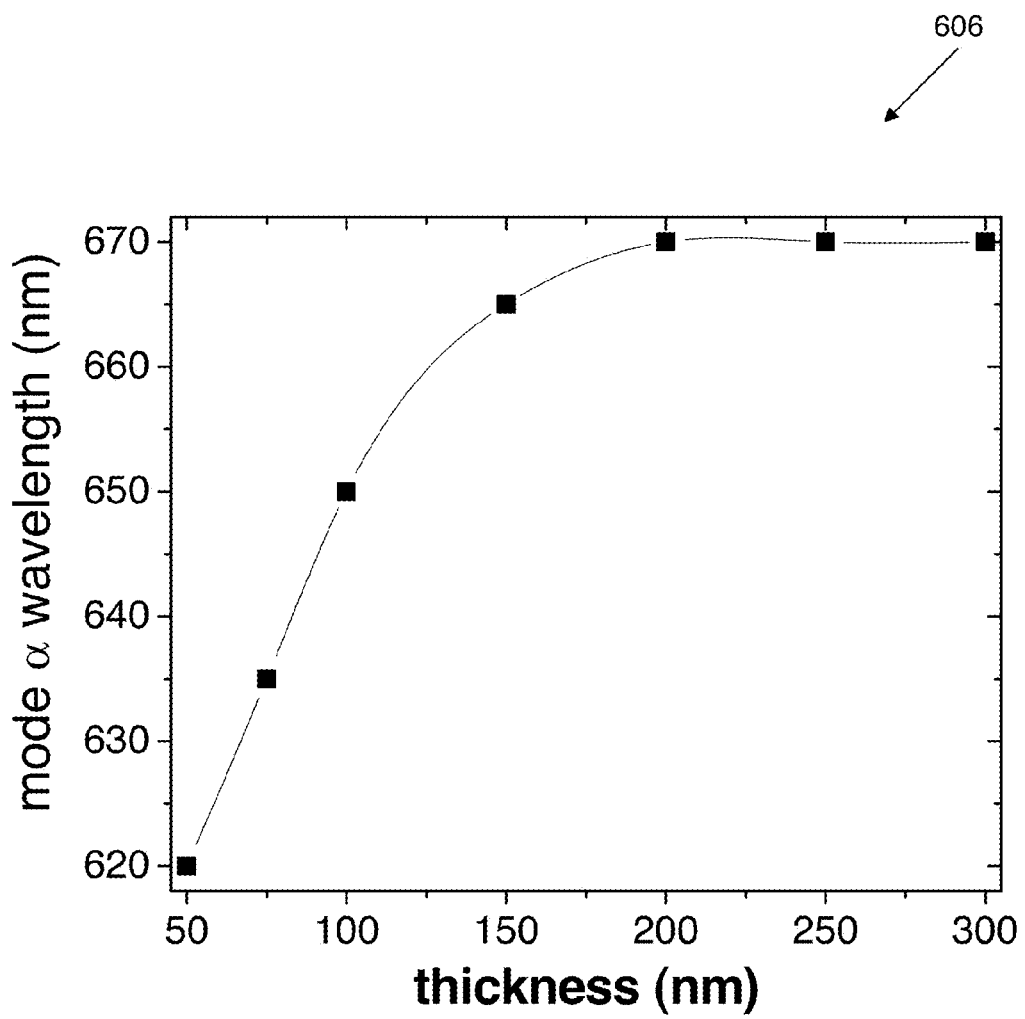
FIG. 6c shows a graph of a resonant wavelength of surface plasmon mode $\alpha$ plotted against a thickness of a layer of a sensor according to one embodiment.

FIG. 6c shows a graph 606 of the resonant wavelength of the principal mode α plotted against a thickness of the layer 204. It can be observed from graph 606 that increasing the thickness from 50 nm to 300 nm leads to a resonant wavelength increase of 50 nm.

Comparing graphs 602, 604 and 606, the change in the resonant wavelength resulted from the change in the pitch of the through holes 206 is higher than that resulted from the change in the diameter of the through holes 206 or the change in the thickness of the layer 204. As such, the pitch of the through holes 206 can be varied to adjust the resonant wavelength, and the diameter of the through holes 206 and the thickness of the layer 204 can be used for fine-tuning the resonant wavelength.

An electric field distribution or peak electric field enhancements can correspond to the resonant wavelengths of the principal mode α. As such, the electric field distribution or peak electric field enhancements may be configured based on one or more of the following parameters: the pitch of the through holes 206, the size (e.g. diameter) of the through holes 206 and the thickness of the layer 204 or the depth of the through holes 206. In one embodiment, peak electric field enhancements refer to the electric field enhancements at the edge 312 of the through holes 206 at an interface of the layer 204 and the matrix 222 (see FIG. 3).

Figure 7A:
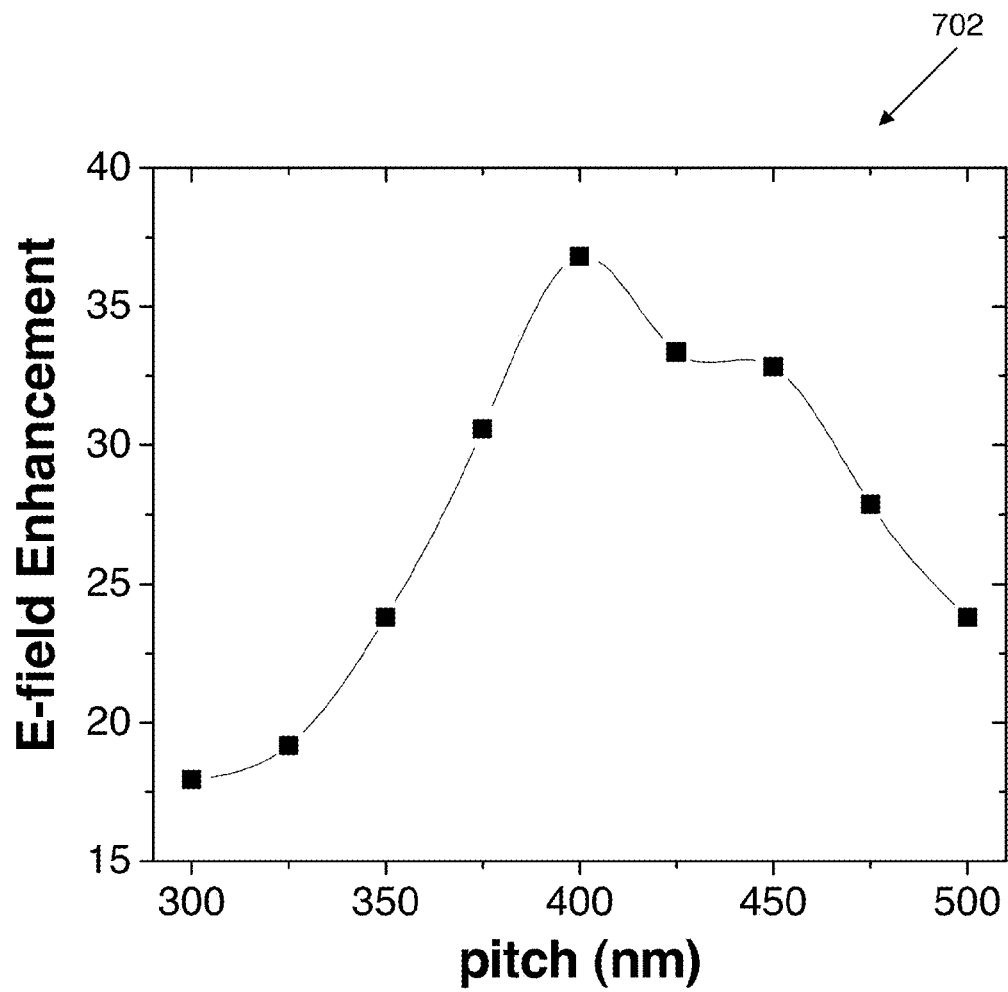
FIG. 7a shows a graph of peak electric field enhancement of surface plasmon mode $\alpha$ plotted against a pitch of through holes of a layer of a sensor according to one embodiment.
Figure 7B:
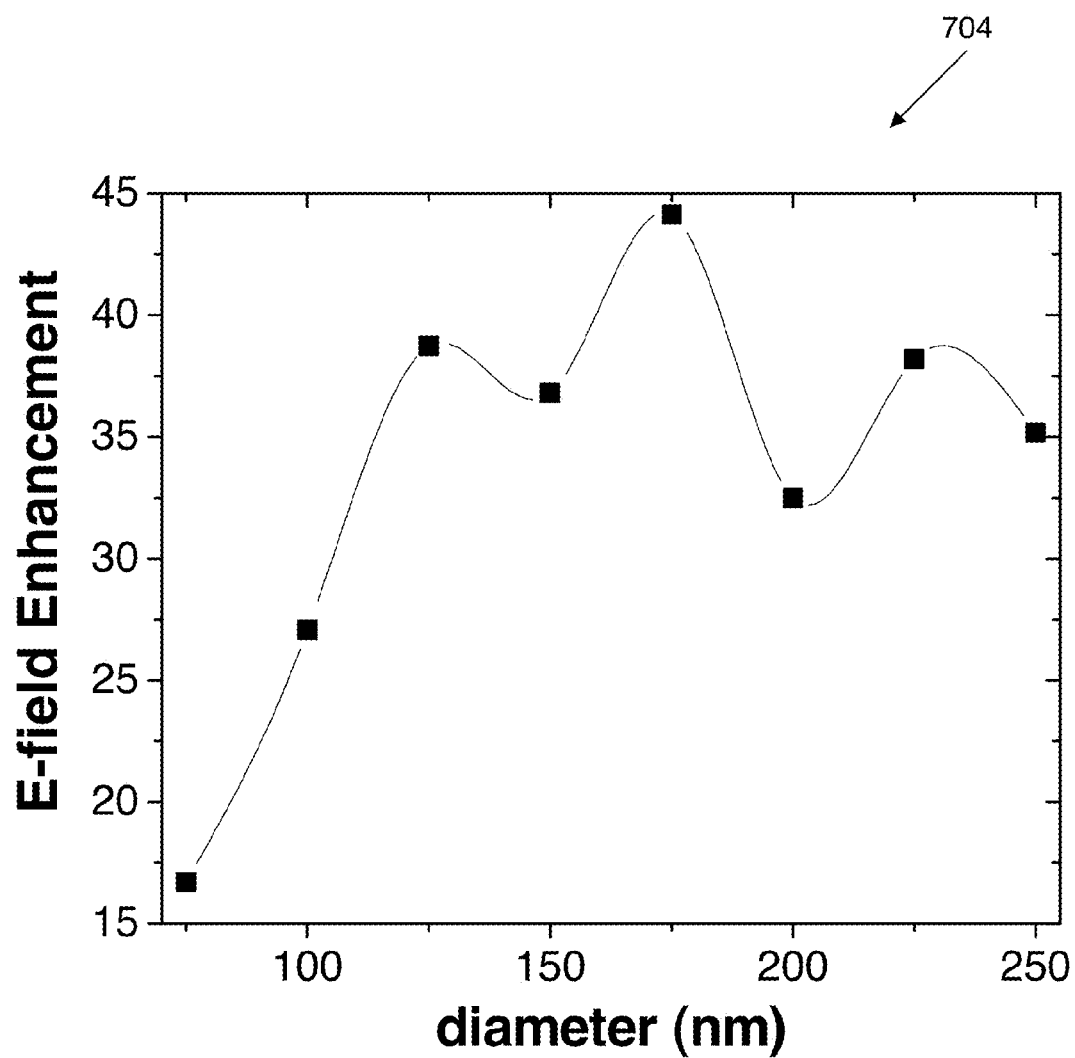
FIG. 7b shows a graph of peak electric field enhancement of surface plasmon mode $\alpha$ plotted against a diameter of through holes of a layer of a sensor according to one embodiment.
Figure 7C:
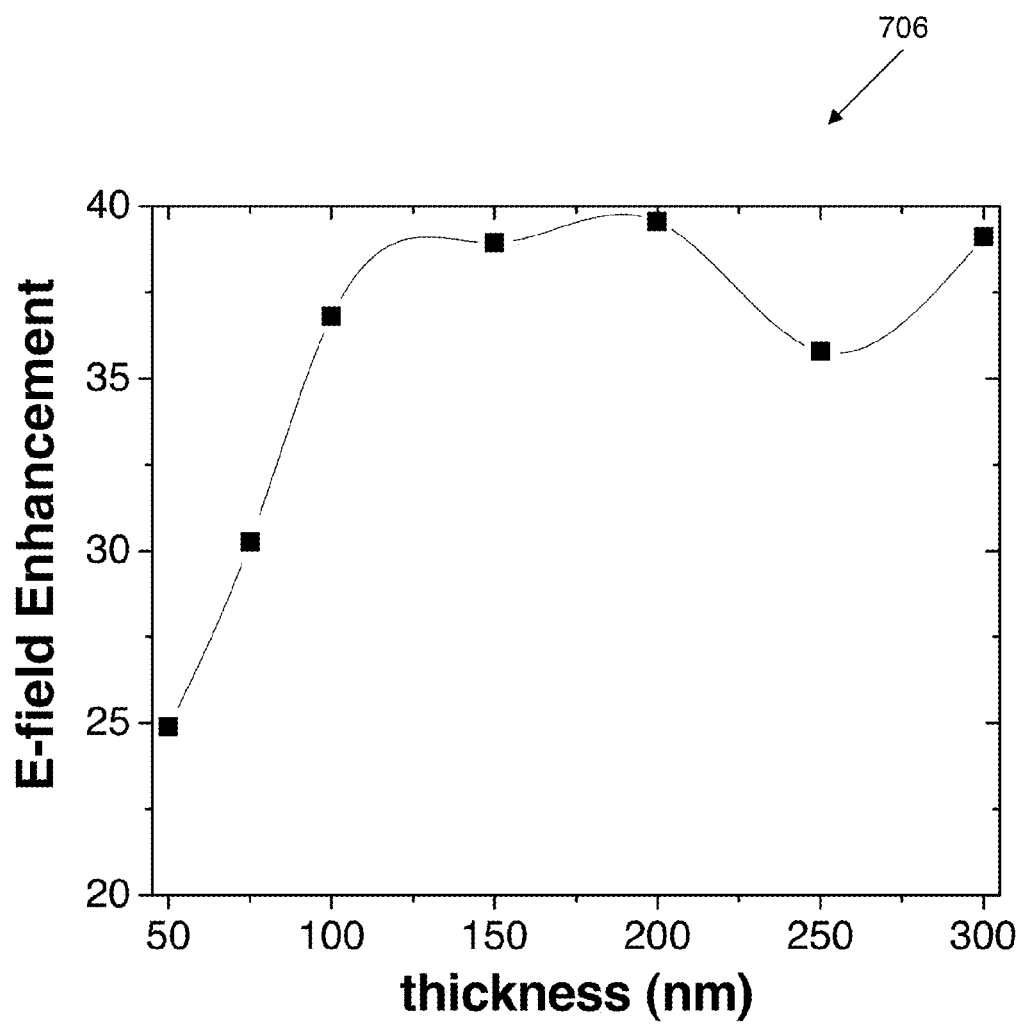
FIG. 7c shows a graph of peak electric field enhancement of surface plasmon mode α plotted against a thickness of a layer of a sensor according to one embodiment.

FIG. 7a shows a graph 702 of the peak electric field enhancement of the principal mode α plotted against a pitch of the through holes 206. FIG. 7b shows a graph 704 of the peak electric field enhancement of the principal mode α plotted against a diameter of the through holes 206. FIG. 7c shows a graph 706 of the peak electric field enhancement of the principal mode α plotted against a thickness of the layer 204. It can be observed from graphs 702, 704 and 706 that the peak electric field enhancement is varied at different resonant wavelengths. This can allow a desired electric field distribution to be selected to meet requirements of the second element 210.

Thus, the LSPR can be tuned by varying the parameters of the layer 204 (e.g. the pitch of the through holes 206, the size (e.g. diameter) of the through holes 206 and the thickness of the layer 204 or the depth of the through holes 206). The desired resonant wavelength and electric field distribution can be chosen to maximize the performance of the second element 210 (which can enhance the LSPR) and hence, improve the sensitivity of the sensor 200.

Further, the sensitivity of the sensor 200 can also be improved by optimizing the positions of the second element 210 (e.g. the positions of the label 306 of the second element 210). At the resonant wavelength, the electric field may not be enhanced equally throughout the whole layer 204. The electric field enhancement may be the highest near the rim of the through holes 206. Since the label 306 of the second element 210 has its own emission characteristics, the positions of the second element 210 (e.g. the positions of the label 306 of the second element 210) can affect the performance (e.g. sensitivity) of the sensor 200.

The emission of the label 306 of the second element 210 can be optimized by adjusting a thickness of the brush polymer 302 of the first element 208 and/or arranging the second element 210 (e.g. the label 306 of the second element 210) at different locations of the sensor 200.

A thickness of the brush polymer 302 of the first element 208 can be obtained by controlling the synthesis process (e.g. controlling the synthesizing time of the brush polymer 302). Alternatively, a desired thickness of the brush polymer 302 can be chosen.

Figure 8:
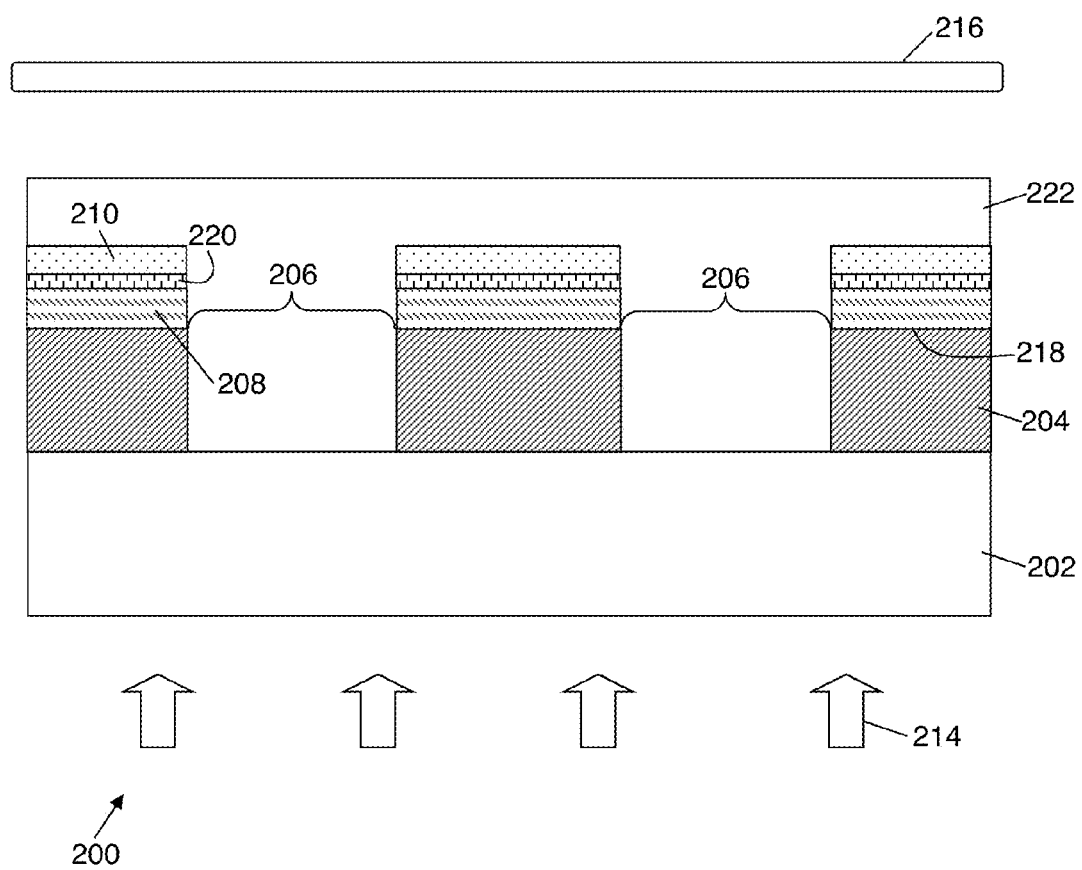
FIG. 8 shows a cross-sectional view of a sensor according to one embodiment.

The second element 210 (e.g. the label 306 of the second element 210) can be arranged at positions with the highest electric field enhancement. In one embodiment, the first element 208 and the second element 210 are arranged within the through holes 206 of the layer 204 as shown in FIG. 2c and FIG. 3. In another embodiment, the first element 208 and the second element 210 can be arranged above the surface 218 of the layer 204 facing away from the substrate 202 as shown in FIG. 8.

Figure 9:
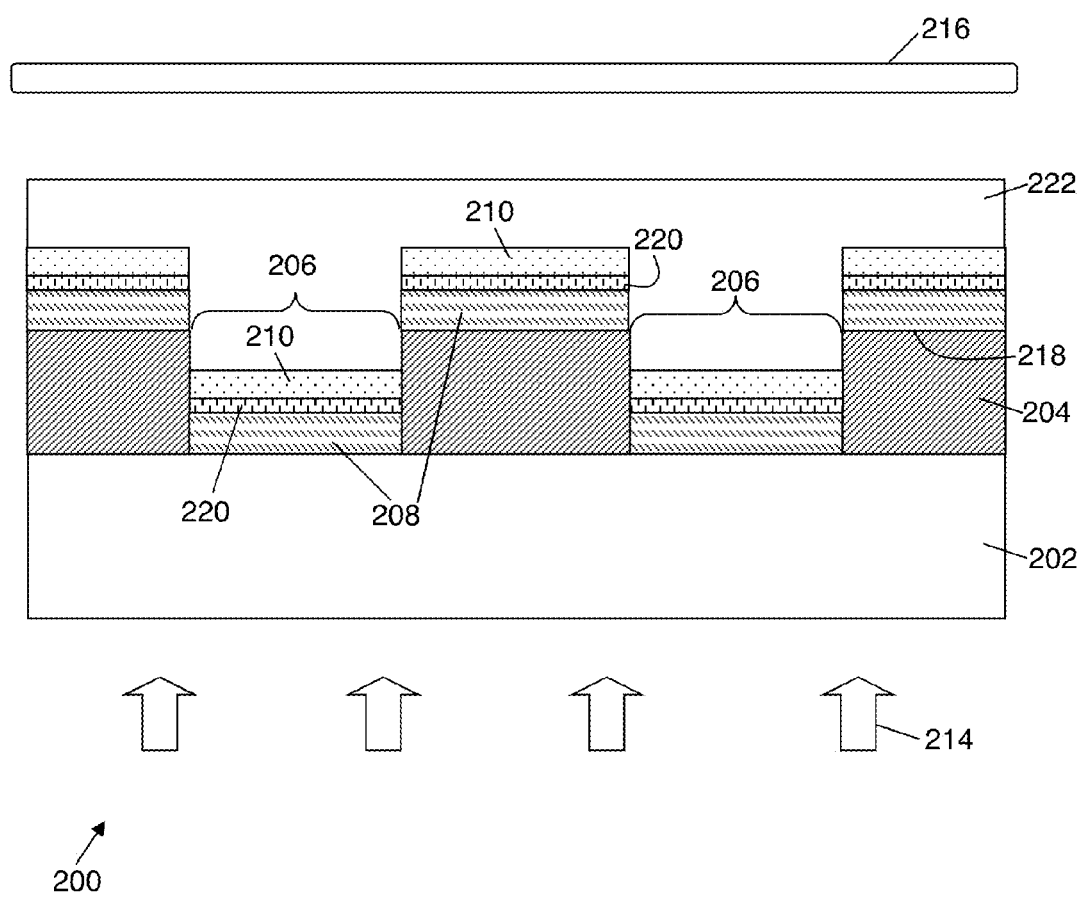
FIG. 9 shows a cross-sectional view of a sensor according to one embodiment.

In another embodiment, as shown in FIG. 9, the first element 208 and the second element 210 can be arranged above the surface 218 of the layer 204 facing away from the substrate 202 and within the through holes 206 of the layer 204.

Figure 10:
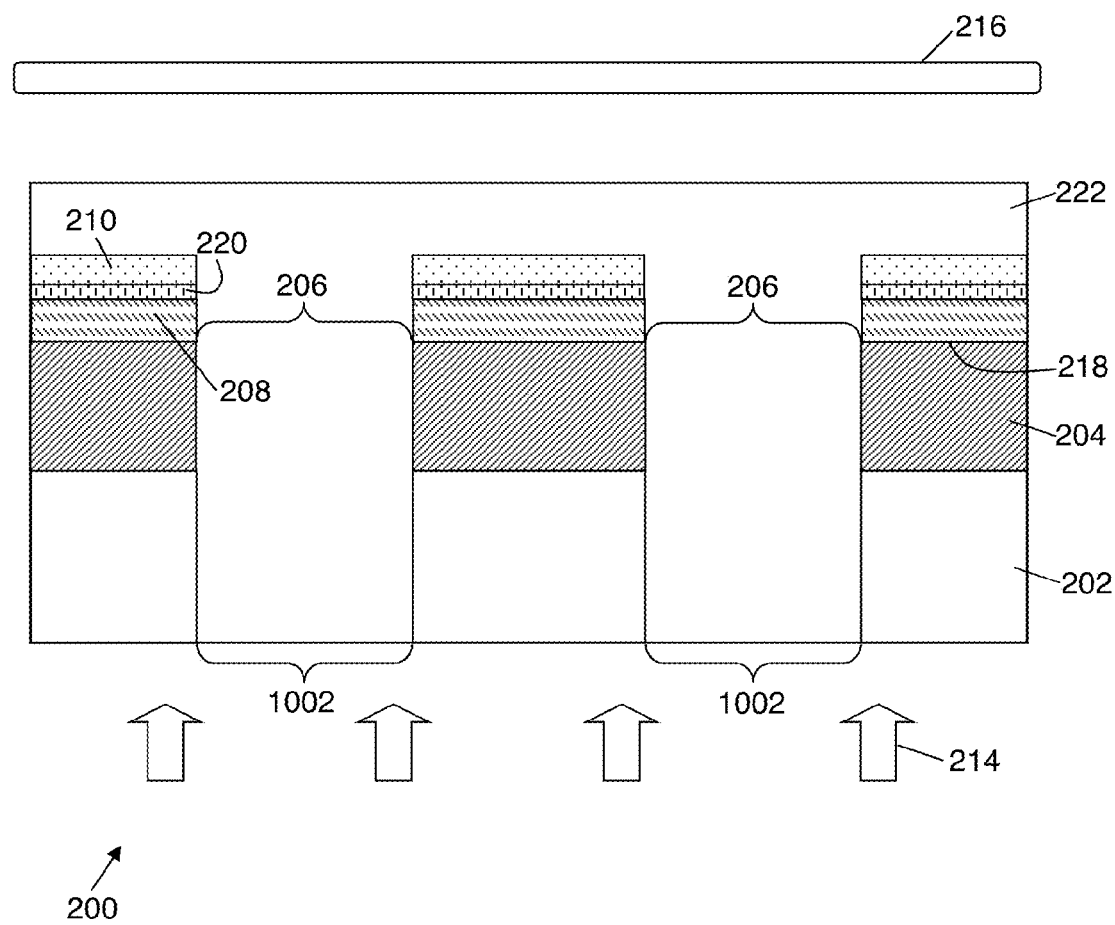
FIG. 10 shows a cross-sectional view of a sensor according to one embodiment.

In another embodiment, as shown in FIG. 10, the substrate 202 includes through holes 1002 which are aligned with the through holes 206 of the layer 204. The first element 208 and the second element 210 are arranged above the surface 218 of the layer 204 facing away from the substrate 202.

The detection sensitivity of the sensor 200 can be improved by adjusting the thickness of the brush polymer 302 and/or arranging the second element 210 (e.g. the label 306 of the second element 210) at locations of the sensor 200 having the highest electric field enhancement.

The sensor 200 as described above can use a [molecular recognition element (first element 208)]-target analyte 220-[signal enhancement element (second element 210)] sandwich structure to improve its sensitivity. As shown in FIGS. 1a to 1c, the spectral shift caused by a small molecule (e.g. target analyte) like PSA is very small and needs a comprehensive detection mechanism to recognize it. With a signal enhancement element (e.g. second element 210) including e.g. fluorescence dyes to amplify the optical signal in the presence of the small molecule, the sensor 200 can detect small molecules (e.g. target analyte) in the sandwich structure even at very low concentrations with an inexpensive optical detector.

The sensor 200 can use dark-field detection to reduce the requirements for light sources and to enhance the signal-to-noise ratio. The signal enhancement element (e.g. second element 210) in the sandwich structure can be excited by the plasmonic resonance that is generated with the nanohole metallic structure (e.g. layer 204 having through holes 206), rather than by the light source 214. The nanohole metallic structure (e.g. layer 204 having through holes 206) can offer LSPR tunability to exactly match the excitation wavelength of the signal enhancement element (e.g. second element 210). The plasmonic resonance can be tunable by changing the shape, size and the pitch of the nanohole structure (e.g. through holes 206). This tunability can enable the signal enhancement element (e.g. second element 210) to be excited exactly at the desired wavelength at which the best emission can be achieved. As such, any light source with the spectra covering the resonant wavelength can be used. There is no need to use expensive laser sources. Further, the dark-field detection can achieve very high signal-to-noise ratio as the reflection and transmission power are excluded.

Further, the sensor 200 can allow target analytes 220 to be bound at preferred locations on the patterned metallic film (e.g. layer 204) to maximize the performance of the sensor 200. The target analytes 220 can be bound to the substrate 202 within the through holes 206, to the surface 218 of the layer 204, or to both via the molecular recognition element (e.g. first element 210). The thickness or dimension of the molecular recognition element (e.g. first element 210) can be selected by controlling the process of its synthesis. As such, the target analyte 220 or the bound signal enhancement element (e.g. second element 210) can be located anywhere near the patterned metallic film (e.g. layer 204). Knowing the electric-field distribution pattern around the patterned metallic film (e.g. layer 204), the signal enhancement element (second element 210) can be positioned at preferred locations where the best performance of the sensor 200 can be achieved.

Instead of using a bulky prism, the sensor 200 can use a nanohole metallic structure (layer 204) and a small and inexpensive light source 214 which make the sensor 200 portable. The sensor 200 also uses a simple detection method due to the adoption of the signal enhancement element (e.g. second element 210). Thus, it is possible to design a multi-channel, high-throughput, and point-of-care sensor system which may require small volume of sample.

There are conventional systems that use aluminum nanoholes to detect fluorescence dyes tagged DNA. Light is illuminated from the substrate side and is detected in reflection mode at the same side. Thus, a fluorescence detection cube has to be used in these conventional systems. The dyes are mainly excited by the light source, and the illumination light needs to be optimized for the specific dye excitation. In contrast, the sensor 200 does not use a fluorescence detection cube. Instead, the sensor 200 uses a [molecular recognition element (first element 208)]-target analyte 220-[signal enhancement element (second element 210)] sandwich structure. In addition, the sensor 200 uses LSPR instead of a light source to generate detection signals.

In another conventional system, gold nanoholes are utilized to enhance the excitation of fluorescence dyes and quantum dots. Laser is used to directly excite the dyes in transmission mode, and the dyes are coated on the nanoholes with no analyte molecular detection involved. In a different conventional system, a single aluminum nanohole of a rectangular or round shape is used to enhance the fluorescence emission. Laser is used to excite the fluorescence dyes, and only the fluorescent dyes are detected in reflection mode. On the contrary, the sensor 200 uses white light and [molecular recognition element (first element 208)]-target analyte 220-[signal enhancement element (second element 210)] sandwich structure to detect the target analyte 220.

In yet another conventional system, fabricated periodic and non-periodic gold nanoholes are used to enhance the fluorescence excitation. Laser is used, and the signal is interrogated with light incident angle variation. Egg-white avidin labeled with fluorescing dye is detected.

However, no [molecular recognition element (first element 208)]-target analyte 220-[signal enhancement element (second element 210)] sandwich structure is used. Other conventional methods may model fluorescence enhancement of nanoholes using only a single nanohole. On the contrary, the sensor 200 uses a nanohole array (e.g. plurality of through holes 206).

In summary, the sensor 200 can be used for detecting small molecules with high sensitivity. The sensor 200 can be manufactured at low cost. The sensor 200 can use a metallic film patterned with nanoholes or nanohole array (e.g. layer 204 with through holes 206) to generate localized surface plasmon resonance (LSPR) and signal amplification, and may have the potential to be developed into a point-of-care diagnostic system. The sensor 200 can use a signal enhancement element (e.g. second element 210) to amplify the plasmonic signal corresponding to the presence of the molecules. As such, the sensor 200 can achieve improved sensitivity and can exclude the use of expensive optical detector.

The sensor 200 can be applicable in medical diagnostics, environmental monitoring, agriculture pesticide and antibiotic monitoring, food additive testing, airborne biological and chemical agent testing, and real time chemical and biological production process monitoring.

Various embodiments described herein for the sensor 200 also apply analogously for a method of detecting a target analyte.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A sensor, comprising:
a substrate;
a layer comprising a plurality of through holes, wherein the layer is disposed above the substrate;
a first element configured to detect a target analyte; and
a second element that can produce a detectable signal;
wherein the first element and the second element are configured to couple the target analyte between the first element and the second element,
the first element is disposed adjacent to the layer, and
the first element and the second element are arranged within the through holes of the layer.

2. The sensor of claim 1, wherein a sensitivity of the sensor is configured based on one or more of a group consisting of a resonant wavelength of the sensor, an electric field distribution of the sensor and a position of the second element.

3. The sensor of claim 2, wherein the resonant wavelength and the electric field distribution of the sensor are configured based on one or more of a group consisting of a pitch of the through holes of the layer, a size of the through holes of the layer and a thickness of the layer.

4. The sensor of claim 2, wherein the resonant wavelength of the sensor is configured to be equal to an excitation wavelength of the second element.

5. The sensor of claim 2, wherein the second element is arranged at positions with the highest electric field enhancement.

6. The sensor of claim 1, wherein the first element and the second element are arranged above a surface of the layer facing away from the substrate.

7. The sensor of claim 6, wherein the substrate comprises through holes being aligned with the through holes of the layer.

8. The sensor of claim 1, wherein the through holes of the layer are distributed sequentially or randomly.

9. The sensor of claim 1, wherein the second element is configured to detect the target analyte and to produce the detectable signal in response to an excitation of the second element coupling to the target analyte.

10. The sensor of claim 1, wherein the second element comprises a label selected from a group consisting of fluorescence dye and light emitter.

11. The sensor of claim 10, wherein the second element further comprises a linker configured to couple the label to the target analyte.

12. The sensor of claim 1, wherein the detectable signal produced by the second element comprises light.

13. The sensor of claim 1, further comprising:
a light source configured to direct light to the sensor; and
an optical detector configured to detect the detectable signal produced by the second element.

14. The sensor of claim 1, wherein the substrate is transparent.

15. The sensor of claim 1, wherein the layer comprises metal.

16. The sensor of claim 1, wherein the sensor is a plasmonic sensor.

17. A method of detecting a target analyte, the method comprising:
coupling the target analyte between a first element and a second element;
wherein the first element is disposed adjacent to a layer comprising a plurality of through holes,
the first element and the second element are arranged within the through holes of the layer, and
the first element detects the target analyte and the second element produces a detectable signal in response to an excitation of the second element coupling to the target analyte.

* * * * *